United States Patent
Marion et al.

(10) Patent No.: US 10,266,483 B2
(45) Date of Patent: Apr. 23, 2019

(54) PROCESS FOR THE MANUFACTURE OF AN AMINO ESTER

(71) Applicant: RHODIA OPERATIONS, Paris (FR)

(72) Inventors: Philippe Marion, Vernaison (FR); Didier Morvan, Mornant (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 15/037,446

(22) PCT Filed: Nov. 18, 2014

(86) PCT No.: PCT/EP2014/074942
§ 371 (c)(1),
(2) Date: May 18, 2016

(87) PCT Pub. No.: WO2015/071500
PCT Pub. Date: May 21, 2015

(65) Prior Publication Data
US 2016/0289167 A1    Oct. 6, 2016

(30) Foreign Application Priority Data

Nov. 18, 2013 (EP) .................... 13193354

(51) Int. Cl.
*C07C 253/30* (2006.01)
*C07C 227/04* (2006.01)
*C08G 69/44* (2006.01)

(52) U.S. Cl.
CPC .......... *C07C 227/04* (2013.01); *C07C 253/30* (2013.01); *C08G 69/44* (2013.01)

(58) Field of Classification Search
CPC .................. C08G 69/08; C08F 8/46
See application file for complete search history.

(56) References Cited

U.S. PATENT DOCUMENTS

| 2010/0168453 | A1 | 7/2010 | Dubois |
| 2011/0224454 | A1 | 9/2011 | Dubois |
| 2013/0116458 | A1 | 5/2013 | Couturier et al. |
| 2015/0011725 | A1* | 1/2015 | Rajendran ............ C08G 69/04 528/310 |

FOREIGN PATENT DOCUMENTS

WO   WO 2013/136111   *  9/2013

OTHER PUBLICATIONS

Borgstrom et al (Randomization of glyceride fatty acids during absorption from the small intestine of the rat, J. Biol. Chem. 1955, 214:671-675, published on May 1955.*

* cited by examiner

*Primary Examiner* — Gregory Listvoyb

(57) ABSTRACT

Process for the manufacture of an amino ester of formula (I) $R_1$—O—C(O)—$(CH_2)_n$—$NH_2$ (I) in which n is an integer from 10 to 15 from an unsaturated ester responding to formula (II) $R_1$—O—C(O)—$(CH_2)_m$—CH=CH—$R_2$ (II) in which $R_1$ is either H or a saturated alkyl group containing from 1 to 5 carbon atoms; $R_2$ is either H or an alkyl group containing from 1 to 10 carbon atoms, either saturated or containing 1 or 2 unsaturations and bearing optionally a hydroxyl, a carboxylic or an ester group, and m is equal to 7, 8, 9, 10 or 11; said process comprising: submitting the unsaturated ester of formula (II) to a catalytic cross-metathesis reaction with a pentenenitrile chosen among 2-pentenenitrile or 3-pentenenitrile in order to obtain a ester-nitrile responding to formula (III) $R_1$—O—C(O)—$(CH_2)_m$—CH=CH—$(CH_2)_p$—CN (III) in which m is equal to 7, 8, 9, 10 or 11 and p is equal to 0 or 1, and submitting the obtained ester-nitrile of formula (III) to an hydrogenation in order to obtain the amino ester of formula (I).

9 Claims, No Drawings

PROCESS FOR THE MANUFACTURE OF AN AMINO ESTER

This application is a U.S. national phase entry under 35 U.S.C. § 371 of International Application No. PCT/EP2014/074942, filed on Nov. 18, 2014, which claims priority to European application No. 13193354.1, filed on Nov. 18, 2013. The entire contents of these applications are explicitly incorporated herein by this reference.

The present invention relates to a process for the manufacture of an amino ester, particularly of an amino ester which is a monomer for the manufacture of polyamide.

Polyamides 11 to 16, respectively also called Nylons 11 to 16, preferably polyamide 11 (PA11) and polyamide 12 (PA12), are high value polymers characterized by high performances. They are prepared by polycondensation of specific monomers, preferably 11-aminoundecanoic acid or ester for PA11 and laurolactam (cyclododecanone lactam) or 12-aminododecanoid acid or ester for PA12.

On a first side, even if the actual industrial route to PA11 monomer presents the advantage of being biobased, it is a highly complex monomer synthesis. Indeed, it starts from castor oil (non-food natural resource) but implies a high number of steps. First of all, castor oil is transesterified into methyl ricinoleate, a rather exotic fatty acid derivative, and glycerol. High temperature treatment at 550° C. of methyl ricinoleate produces then methyl 11-undecenoate and heptanal which are separated. Hydrolysis of methyl 11-undecenoate leads to 11-undecanoic acid which after hydrobromination leads to 11-bromoundecanoic acid and after reaction with ammonia, 11-aminoundecanoic acid, the monomer used to make PA11, is finally obtained.

While this process performed industrially for several decades is satisfactory on the whole, it presents a certain number of drawbacks, notably the fact that its implementation is in practice governed by access to a specific raw material, castor oil, which further contains a toxin (ricin) which is extremely toxic and is therefore necessary to remove. Other drawbacks are that the reagents used (ammonia and bromine) require expensive precautions for storage and use, that the process generates high quantities of salt (NaBr) and that the process is characterized by high environmental constraints. Another disadvantage is that the process coproduces heptanal in high volumes with difficulties linked to the fact that the market for heptanal is small. A final drawback is that such process involves a high number of steps and is therefore very complex and costly.

Solutions in order to avoid such drawbacks have already been proposed. In particular, FR 2912741 A1 has proposed a process for synthesizing amino acids or amino esters from monounsaturated long-chain natural fatty acids or esters comprising at least one step of metathesis. This document describes notably a process directed toward to the synthesis of 11-aminoundecanoic acid from oleic acid which consists, in a first step, in reacting oleic acid or its esters with acrylonitrile, and then, in a second step, in subjecting the product resulting from this first step to a hydrogenation to produce 11-aminoundecanoic acid.

The process according to this document presents however the great drawback that acrylonitrile is not only a CMR (Carcinogenicity, Mutagenicity, Reproductive toxicity) chemical product, in particular is carcinogeous and highly toxic, but also that it is characterized by a very high vapor tension and by a very low flash point and low boiling point and by an instability (particularly to light radiation) rendering its use very difficult, highly dangerous and unsafe.

On another side, the actual industrial route to PA12 monomer is also a highly complex monomer synthesis which requires 6 steps. Indeed, it starts from three butadiene molecules which are cyclotrimerized into cyclododecatriene, afterwards hydrogenated into cyclododecane, then oxidized into cyclododecanol which is submitted to dehydrogenation into cyclododecanone, afterwards submitted to oximation into cyclododecanone oxime and Beckmann transposition into cyclododecananone lactam which is laurolactam. This process presents further the disadvantages of not involving biosourced resource and of being costly due to the starting material (butadiene) price.

It therefore remains a need in finding a process which allows the manufacture of amino esters, in particular amino esters which are monomers for the manufacture of polyamides, which does not present the drawbacks detailed above. Applicant has found in this context a new process for the manufacture of amino esters.

Hence, a first aspect of the present invention concerns mainly a process for the manufacture of an amino ester of formula (I)

$$R_1-O-C(O)-(CH_2)_n-NH_2 \tag{I}$$

in which n is an integer from 10 to 15
from an unsaturated ester responding to formula (II)

$$R_1-O-C(O)-(CH_2)_m-CH=CH-R_2 \tag{II}$$

in which
$R_1$ is either H or a saturated alkyl group containing from 1 to 5 carbon atoms;
$R_2$ is either H or an alkyl group containing from 1 to 10 carbon atoms, either saturated or containing 1 or 2 unsaturations and bearing optionally a hydroxyl, a carboxylic or an ester group, and
m is equal to 7, 8, 9, 10 or 11;
said process comprising
submitting the unsaturated ester of formula (II) to a catalytic cross-metathesis reaction with a pentenenitrile chosen among 2-pentenenitrile or 3-pentenenitrile in order to obtain a ester-nitrile responding to formula (III)

$$R_1-O-C(O)-(CH_2)_m-CH=CH-(CH_2)_p-CN \tag{III}$$

in which m is equal to 7, 8, 9, 10 or 11 and p is equal to 0 or 1, and
submitting the obtained ester-nitrile of formula (III) to an hydrogenation in order to obtain the amino ester of formula (I).

The process according to the invention comprises submitting an unsaturated ester responding to formula (II)

$$R_1-O-C(O)-(CH_2)_m-CH=CH-R_2 \tag{II}$$

in which
$R_1$ is either H or a saturated alkyl group containing from 1 to 5 carbon atoms;
$R_2$ is either H or an alkyl group containing from 1 to 10 carbon atoms, either saturated or containing 1 or 2 unsaturations and bearing optionally a hydroxyl, a carboxylic or an ester group, and
m is equal to 7, 8, 9 or 11;
to a catalytic cross-metathesis reaction with a pentenenitrile chosen among 2-pentenenitrile or 3-pentenenitrile in order to obtain a ester-nitrile responding to formula (III)

$$R_1-O-C(O)-(CH_2)_m-CH=CH-(CH_2)_p-CN \tag{III}$$

in which m is equal to 7, 8, 9 or 11 and p is equal to 0 or 1.

The cross-metathesis reaction is a catalytic reaction involving advantageously the rupture and the reformation of carbon-carbon double bonds.

The cross-metathesis reaction is advantageously carried out by homogeneous catalysis, preferably by using a ruthenium based homogeneous catalyst, more preferably s ruthenium base homogeneous catalyst among the ones represented by the formulas here after in which Cy is cyclohexyl, DIPP is diisopropylphenyl, Et is ethyl, i-Bu is isobutyl, iPr is isopropyl, Mes is mesityl, Ph is phenyl and TsO is tosyl.

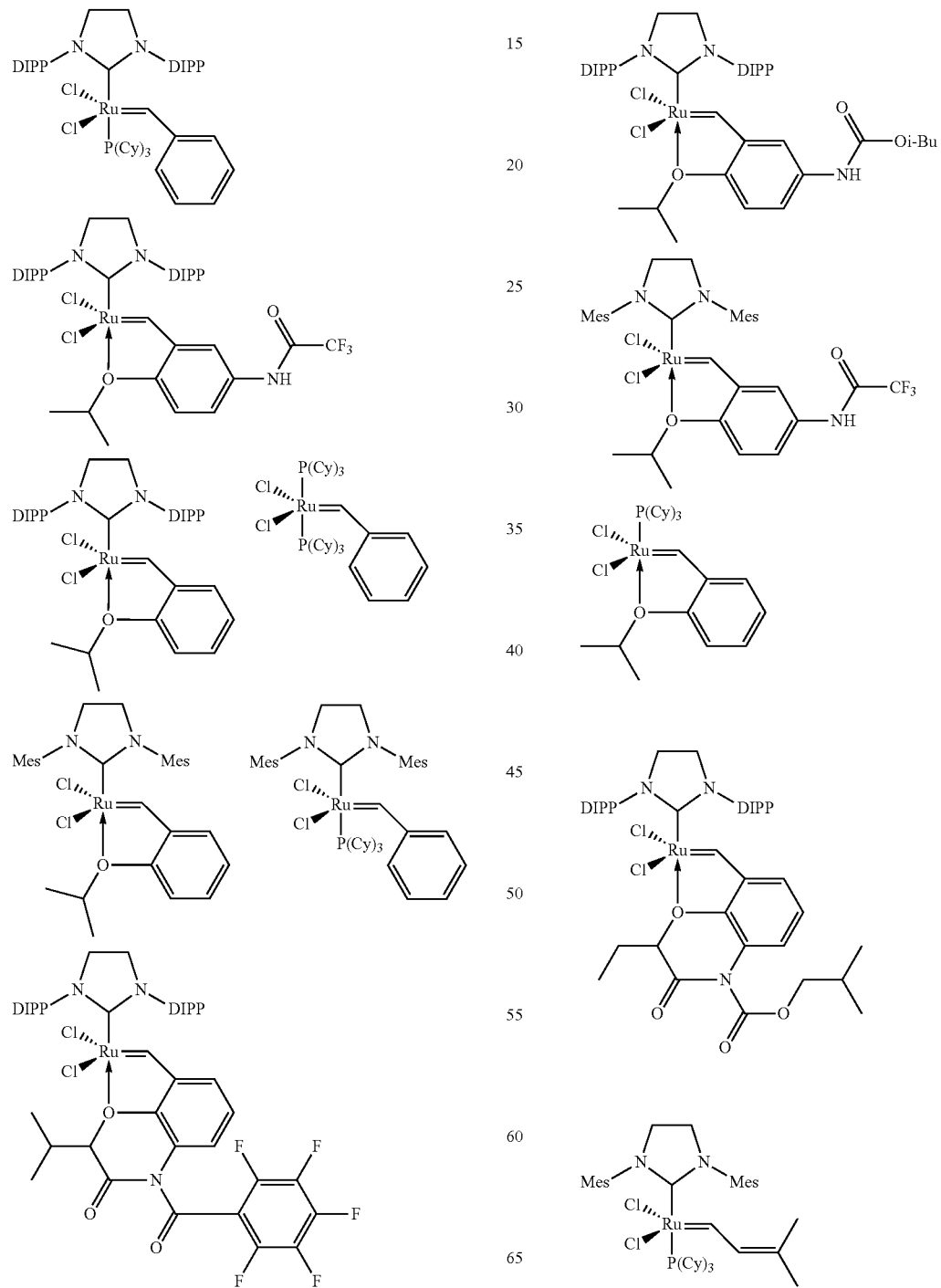

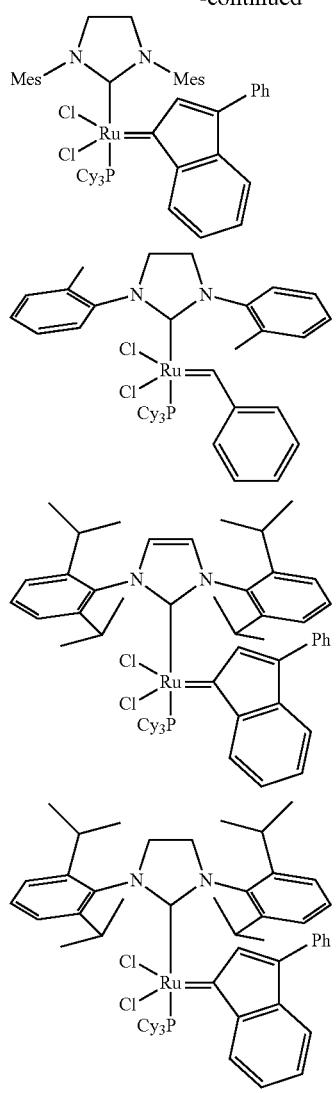
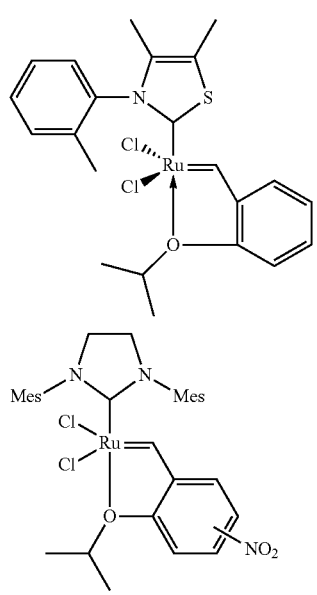
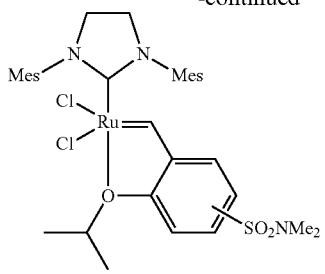
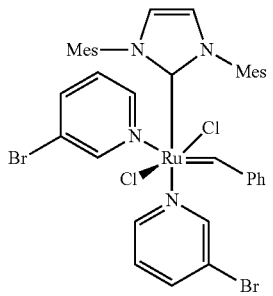
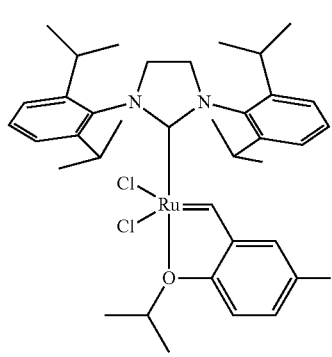
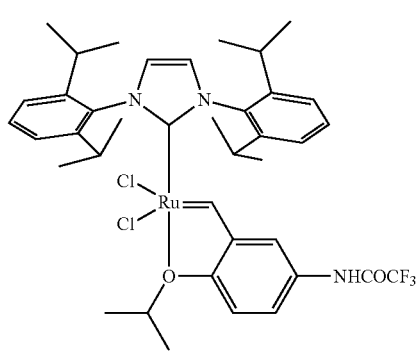
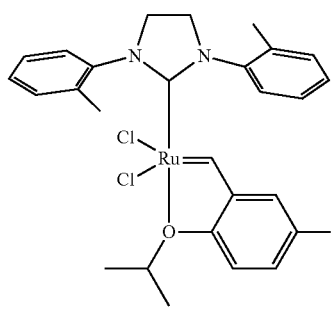

-continued
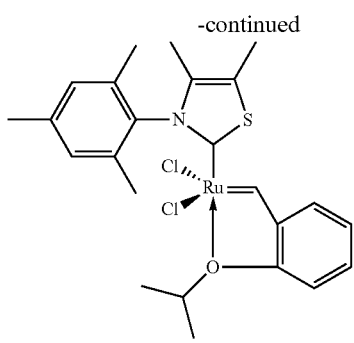
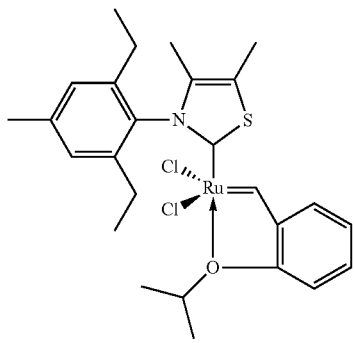
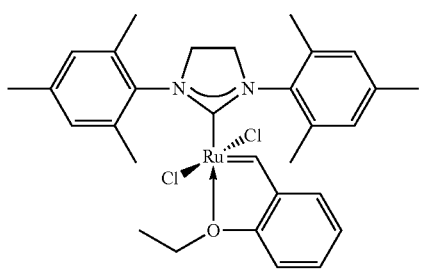
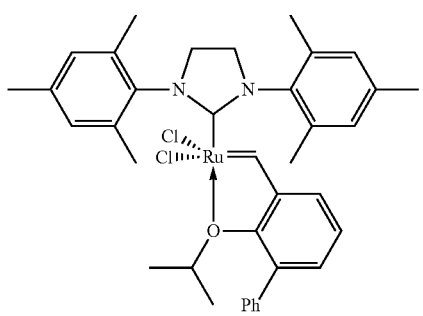
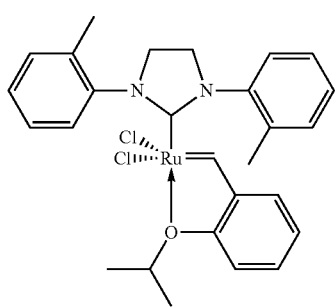
-continued
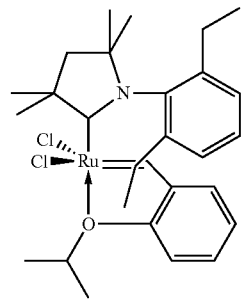
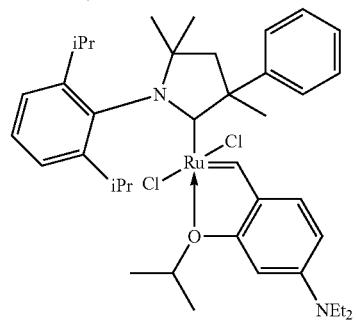
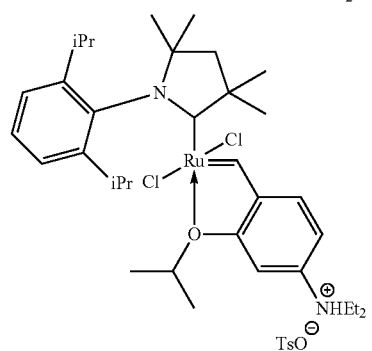
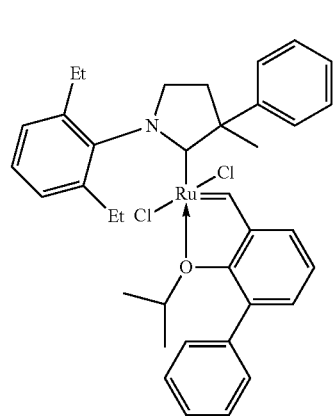
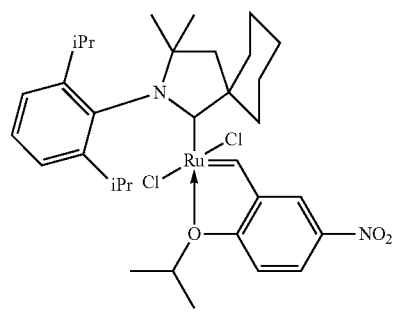

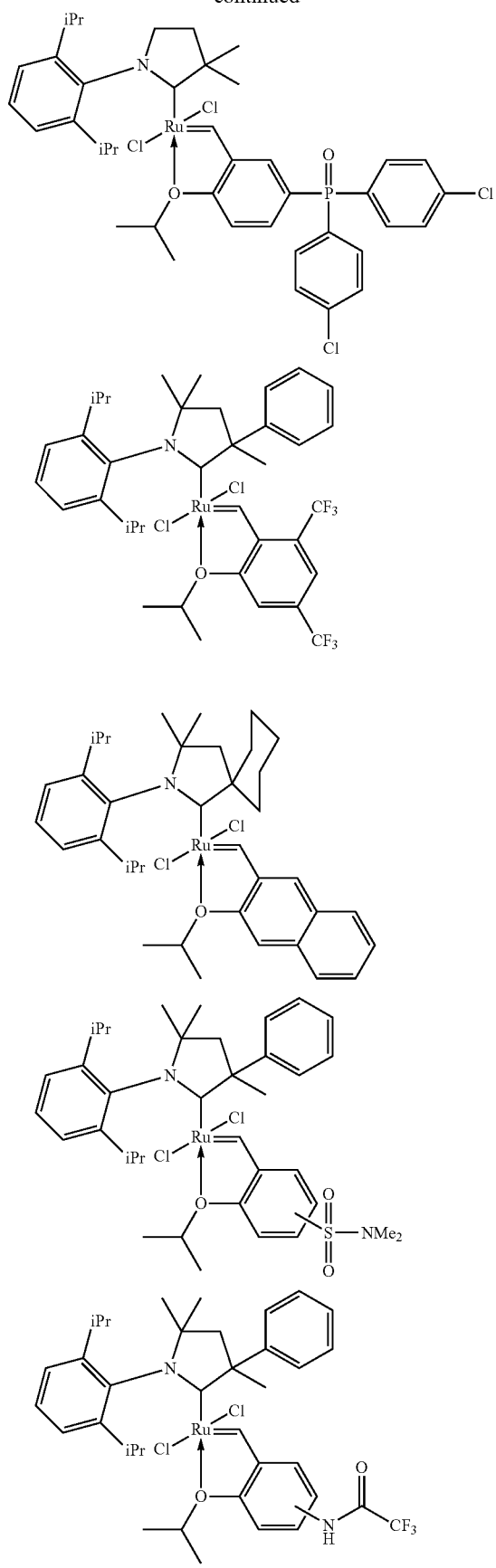
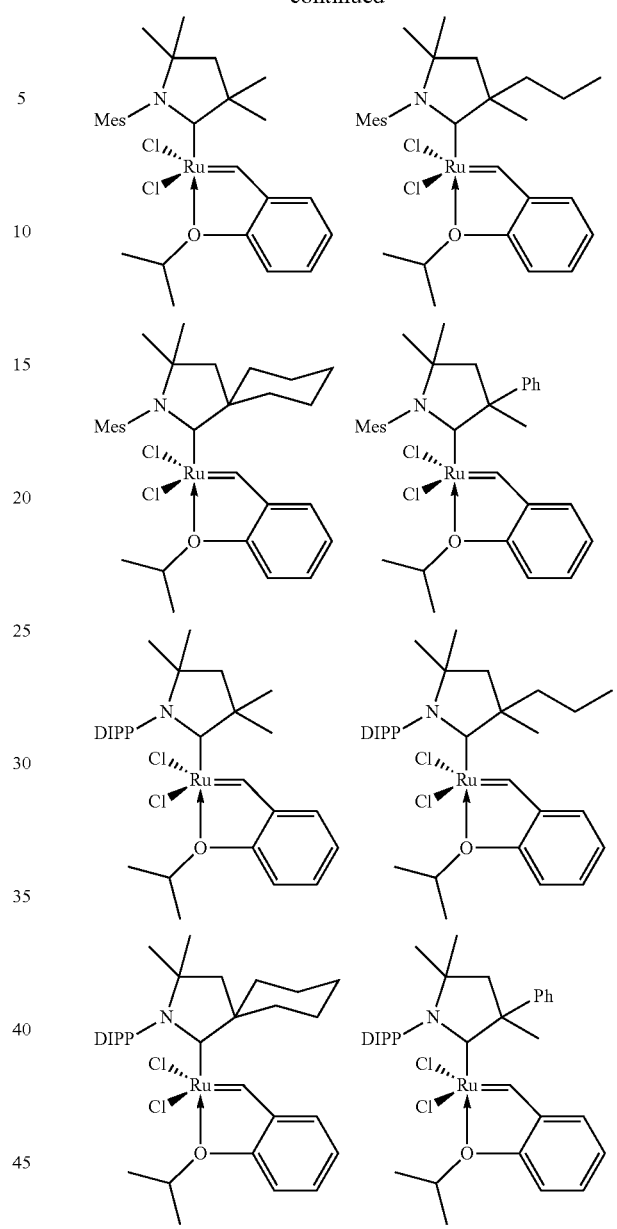
The cross-metathesis reaction is more preferably carried out by homogeneous catalysis using the ruthenium based homogeneous catalyst represented by the formulas here after in which Cy is cyclohexyl, DIPP is diisopropylphenyl, Mes is mesityl and Ph is phenyl.
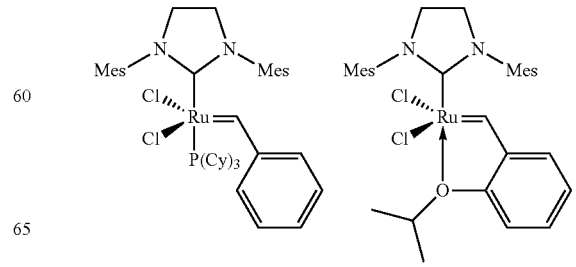

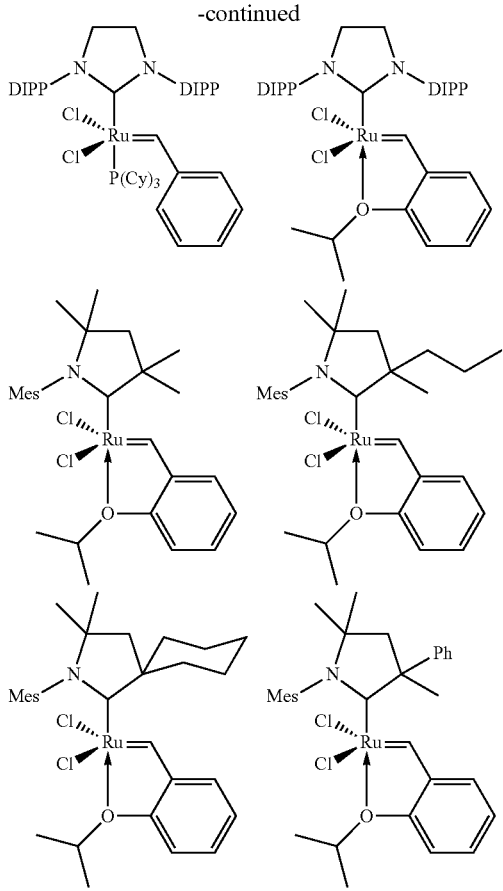

The catalytic cross-metathesis reaction is advantageously conducted in mild conditions.

The temperature of such reaction is advantageously low. The temperature of the reaction is advantageously from 0 to 200° C., preferably from 20 to 150° C., more preferably from 25 to 130° C. and still more preferably from to 60 to 110° C.

The catalytic cross-metathesis reaction can be performed at any pressure, advantageously from 1 bar to 40 bar. Preferably it is performed at atmospheric pressure i.e. 1 bar.

The catalytic cross-metathesis reaction is performed with a molar ratio between the pentenenitrile and the unsaturated ester responding to formula (II) advantageously from 0.8 to 10, preferably from 0.9 to 7 and more preferably from 1 to 4.

The catalytic cross-metathesis reaction is performed with a catalyst molar content advantageously from 0.0001 to 20% mol, preferably from 0.0005 to 2% mol and more preferably from 0.001 to 1.5% mol, compared to the unsaturated ester of formula (II) molar content.

The catalytic cross-metathesis reaction is advantageously performed in inert atmosphere (like under nitrogen or argon). Preferably, it is done under inert atmosphere of argon.

The catalytic cross-metathesis reaction can be performed in the presence of a solvent or not.

All organic solvents which dissolve the catalytic system are suitable for the process according to the invention. In particular, solvent could be one of the following list: benzene, toluene, xylenes (para, ortho and meta), chlorobenzene, dichlorobenzene, cyclopentane, n-pentane, cyclohexane, n-hexane, n-heptane, dichloromethane, dichloroethane, chloroform, diethylether, diphenylether, dioxane, tetrahydrofurane, ethyl acetate, butyl acetate, acetone, acetonitrile, dimethylsulfoxide, methanol, ethanol, propanol, isopropanol, n-butanol, iso-butanol, n-pentanol and n-hexanol. Preferably, the solvent is selected from toluene, xylenes (para, ortho and meta), chlorobenzene, dichlorobenzene, cyclohexane, n-hexane, n-heptane, dichloromethane, dichloroethane, chloroform, diethylether, tetrahydrofurane, ethyl acetate, acetone and acetonitrile. More preferably the solvent is selected from toluene, xylenes (para, ortho and meta), cyclohexane, n-hexane, dichloromethane, chloroform, tetrahydrofurane, ethyl acetate and acetonitrile.

Different equipments can be used to carry out the catalytic cross-metathesis reaction.

Tubular, stirred, isothermal or adiabatic reactors can be used.

Skilled in the art can choose the mobile and the injection configuration to introduce reactants and catalyst in function of the process constraint.

The dissipated power is comprised advantageously between 50 and 3000 W/m$^3$ and preferably between 100 and 1500 W/m$^3$.

The reactor can be advantageously preceded by a static mixer (like Sulzer SMX, SMV, Kenics, . . . ) or a dynamic like venturi ejector or co axial jets or impinging jets or swirl to mix catalyst, for instance Hartridge Roughton, star laminator ou slit interdigital (IMM).

A recycling of the co-products formed is advantageously performed. In such case, they are preferably separated by a common process unit (distillation, membrane separation . . . ) and recycled to the catalytic cross-metathesis reaction. Co-products formed are usually unsaturated nitriles, unsaturated dinitriles, unsaturated esters, unsaturated diesters and olefins with different chain length depending on the nature of the starting unsaturated ester of formula (II) and of the pentenenitrile used.

Advantageously, the process according to the invention comprises only one catalytic cross-metathesis reaction.

Advantageously, in the process according to the invention, the unsaturated ester of formula (II) is obtained by a reaction other than a catalytic cross-metathesis reaction.

The unsaturated ester, also called unsaturated fatty ester, submitted to the catalytic cross-metathesis reaction with the pentenenitrile in the process according to the invention, is an unsaturated ester responding to formula (II)

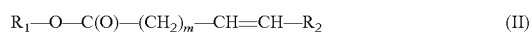

$$R_1-O-C(O)-(CH_2)_m-CH=CH-R_2 \quad (II)$$

in which
R$_1$ is either H or a saturated alkyl group containing from 1 to 5 carbon atoms;
R$_2$ is either H or an alkyl group containing from 1 to 10 carbon atoms, either saturated or containing 1 or 2 unsaturations and bearing optionally a hydroxyl, a carboxylic or an ester group, and
m is equal to 7, 8, 9, 10 or 11;
with the preference that
when m is equal to 7, R$_2$ is either H or an alkyl group containing from 1 to 10 carbon atoms, either saturated or containing 1 or 2 unsaturations and bearing optionally a hydroxyl, a carboxylic or an ester group, with a particular preference when R$_2$ is an alkyl group containing from 2 to 8 carbon atoms, either saturated or containing 1 or 2 unsaturations and bearing optionally a hydroxyl, a carboxylic or an ester group;
when m is equal to 8, R$_2$ is H;

when m is equal to 9, $R_2$ is a saturated alkyl group containing from 6 to 8 carbon atoms;
when m is equal to 10, $R_2$ is a saturated alkyl group containing 5 carbon atoms; and
when m is equal to 11, $R_2$ is a saturated alkyl group containing 8 carbon atoms.

Examples of unsaturated esters responding to such preference are

Myristoleic esters responding to formula $$R_1-O-C(O)-(CH_2)_7-CH=CH-(CH_2)_3-CH_3$$

Palmitoleic esters responding to formula $$R_1-O-C(O)-(CH_2)_7-CH=CH-(CH_2)_5-CH_3$$

Oleic esters (cis isomer) or elaidic esters (trans isomer) responding to formula $$R_1-O-C(O)-(CH_2)_7-CH=CH-(CH_2)_7-CH_3$$

Methyl oleate responding to formula $$CH_3-O-C(O)-(CH_2)_7-CH=CH-(CH_2)_7-CH_3$$

Linoleic esters (cis isomer) or linoelaidic esters (trans isomer) responding to formula $$R_1-O-C(O)-(CH_2)_7-CH=CH-CH_2-CH=CH-(CH_2)_4-CH_3$$

α-Linolenic esters responding to formula $$R_1-O-C(O)-(CH_2)_7-CH=CH-CH_2-CH=CH-CH_2-CH=CH-CH_2-CH_3$$

Ricinoleic esters responding to formula $$R_1-O-C(O)-(CH_2)_7-CH=CH-CH_2-CH(OH)-(CH_2)_5-CH_3$$

Methyl ester of 9-decenoic acid of formula $$CH_3-O-C(O)-(CH_2)_7-CH=CH_2$$

Methyl ester of 9-undecenoic acid of formula $$CH_3-O-C(O)-(CH_2)_7-CH=CH-CH_3$$

Methyl ester of 9-dodecenoic acid of formula $$CH_3-O-C(O)-(CH_2)_7-CH=CH-CH_2CH_3$$

Esters of 9-octadecenedioic acid responding to formula $$R_1-O-C(O)-(CH_2)_7-CH=CH-(CH_2)_7-C(O)-O-R_1$$

Methyl ester of 10-undecenoic acid of formula $$CH_3-O-C(O)-(CH_2)_8-CH=CH_2$$

Vaccenic esters responding to formula $$R_1-O-C(O)-(CH_2)_9-CH=CH-(CH_2)_5-CH_3$$

Gondoïc esters responding to formula $$R_1-O-C(O)-(CH_2)_9-CH=CH-(CH_2)_7-CH_3$$

Octadecenoic esters responding to formula $$R_1-O-C(O)-(CH_2)_9-CH=CH-(CH_2)_5-CH_3$$

Octadecenoic esters responding to formula $$R_1-O-C(O)-(CH_2)_{10}-CH=CH-(CH_2)_4-CH_3$$

Erucic esters responding to formula $$R_1-O-C(O)-(CH_2)_{11}-CH=CH-(CH_2)_7-CH_3$$

The unsaturated ester submitted to the catalytic cross-metathesis reaction with the pentenenitrile in the process according to the invention, is preferably an unsaturated ester responding to formula (II)

$$R_1-O-C(O)-(CH_2)_m-CH=CH-R_2 \quad (II)$$

in which $R_1$ is either H or a saturated alkyl group containing from 1 to 5 carbon atoms;

$R_2$ is either H or an alkyl group containing from 1 to 10 carbon atoms, either saturated or containing 1 or 2 unsaturations and bearing optionally a hydroxyl, a carboxylic or an ester group, and m is equal to 7, 8 or 11;

with the preference that when m is equal to 7, $R_2$ is either H or an alkyl group containing from 1 to 10 carbon atoms, either saturated or containing 1 or 2 unsaturations and bearing optionally a hydroxyl, a carboxylic or an ester group, with a particular preference when $R_2$ is an alkyl group containing from 2 to 8 carbon atoms, either saturated or containing 1 or 2 unsaturations and bearing optionally a hydroxyl, a carboxylic or an ester group;

when m is equal to 8, $R_2$ is H; and when m is equal to 11, $R_2$ is a saturated alkyl group containing 8 carbon atoms.

Examples of unsaturated esters responding to such preference are

Myristoleic esters responding to formula $$R_1-O-C(O)-(CH_2)_7-CH=CH-(CH_2)_3-CH_3$$

Palmitoleic esters responding to formula $$R_1-O-C(O)-(CH_2)_7-CH=CH-(CH_2)_5-CH_3$$

Oleic esters (cis isomer) or elaidic esters (trans isomer) responding to formula $$R_1-O-C(O)-(CH_2)_7-CH=CH-(CH_2)_7-CH_3$$

Methyl oleate responding to formula $$CH_3-O-C(O)-(CH_2)_7-CH=CH-(CH_2)_7-CH_3$$

Linoleic esters (cis isomer) or linoelaidic esters (trans isomer) responding to formula $$R_1-O-C(O)-(CH_2)_7-CH=CH-CH_2-CH=CH-(CH_2)_4-CH_3$$

α-Linolenic esters responding to formula $$R_1-O-C(O)-(CH_2)_7-CH=CH-CH_2-CH=CH-CH_2-CH=CH-CH_2-CH_3$$

Ricinoleic esters responding to formula $$R_1-O-C(O)-(CH_2)_7-CH=CH-CH_2-CH(OH)-(CH_2)_5-CH_3$$

Methyl ester of 9-decenoic acid of formula $$CH_3-O-C(O)-(CH_2)_7-CH=CH_2$$

Methyl ester of 9-undecenoic acid of formula $$CH_3-O-C(O)-(CH_2)_7-CH=CH-CH_3$$

Methyl ester of 9-dodecenoic acid of formula $$CH_3-O-C(O)-(CH_2)_7-CH=CH-CH_2CH_3$$

Esters of 9-octadecenedioic acid responding to formula $$R_1-O-C(O)-(CH_2)_7-CH=CH-(CH_2)_7-C(O)-O-R_1$$

Methyl ester of 10-undecenoic acid of formula $$CH_3-O-C(O)-(CH_2)_8-CH=CH_2$$

Erucic esters responding to formula $$R_1-O-C(O)-(CH_2)_{11}-CH=CH-(CH_2)_7-CH_3$$

The unsaturated ester submitted to the catalytic cross-metathesis reaction with the pentenenitrile in the process according to the invention, is more preferably an unsaturated ester responding to formula (II)

$$R_1\text{—}O\text{—}C(O)\text{—}(CH_2)_m\text{—}CH\text{=}CH\text{—}R_2 \quad (II)$$

in which
$R_1$ is either H or a saturated alkyl group containing from 1 to 5 carbon atoms;
$R_2$ is either H or an alkyl group containing from 1 to 10 carbon atoms, either saturated or containing 1 or 2 unsaturations and bearing optionally a hydroxyl, a carboxylic or an ester group, and
m is equal to 7 or 8;
with the preference that
when m is equal to 7, $R_2$ is either H or an alkyl group containing from 1 to 10 carbon atoms, either saturated or containing 1 or 2 unsaturations and bearing optionally a hydroxyl, a carboxylic or an ester group, with a particular preference when $R_2$ is an alkyl group containing from 2 to 8 carbon atoms, either saturated or containing 1 or 2 unsaturations and bearing optionally a hydroxyl, a carboxylic or an ester group; and
when m is equal to 8, $R_2$ is H.

Examples of unsaturated esters responding to such preference are

Myristoleic esters responding to formula $$R_1\text{—}O\text{—}C(O)\text{—}(CH_2)_7\text{—}CH\text{=}CH\text{—}(CH_2)_3\text{—}CH_3$$

Palmitoleic esters responding to formula $$R_1\text{—}O\text{—}C(O)\text{—}(CH_2)_7\text{—}CH\text{=}CH\text{—}(CH_2)_5\text{—}CH_3$$

Oleic esters (cis isomer) or elaidic esters (trans isomer) responding to formula $$R_1\text{—}O\text{—}C(O)\text{—}(CH_2)_7\text{—}CH\text{=}CH\text{—}(CH_2)_7\text{—}CH_3$$

Methyl oleate responding to formula $$CH_3\text{—}O\text{—}C(O)\text{—}(CH_2)_7\text{—}CH\text{=}CH\text{—}(CH_2)_7\text{—}CH_3$$

Linoleic esters (cis isomer) or linoelaidic esters (trans isomer) responding to formula $$R_1\text{—}O\text{—}C(O)\text{—}(CH_2)_7\text{—}CH\text{=}CH\text{—}CH_2\text{—}CH\text{=}CH\text{—}(CH_2)_4\text{—}CH_3$$

α-Linolenic esters responding to formula $$R_1\text{—}O\text{—}C(O)\text{—}(CH_2)_7\text{—}CH\text{=}CH\text{—}CH_2\text{—}CH\text{=}CH\text{—}CH_2\text{—}CH\text{=}CH\text{—}CH_2\text{—}CH_3$$

Ricinoleic esters responding to formula $$R_1\text{—}O\text{—}C(O)\text{—}(CH_2)_7\text{—}CH\text{=}CH\text{—}CH_2\text{—}CH(OH)\text{—}(CH_2)_5\text{—}CH_3$$

Methyl ester of 9-decenoic acid of formula $$CH_3\text{—}O\text{—}C(O)\text{—}(CH_2)_7\text{—}CH\text{=}CH_2$$

Methyl ester of 9-undecenoic acid of formula $$CH_3\text{—}O\text{—}C(O)\text{—}(CH_2)_7\text{—}CH\text{=}CH\text{—}CH_3$$

Methyl ester of 9-dodecenoic acid of formula $$CH_3\text{—}O\text{—}C(O)\text{—}(CH_2)_7\text{—}CH\text{=}CH\text{—}CH_2CH_3$$

Esters of 9-octadecenedioic acid responding to formula $$R_1\text{—}O\text{—}C(O)\text{—}(CH_2)_7\text{—}CH\text{=}CH\text{—}(CH_2)_7\text{—}C(O)\text{—}O\text{—}R_1$$

Methyl ester of 10-undecenoic acid of formula $$CH_3\text{—}O\text{—}C(O)\text{—}(CH_2)_8\text{—}CH\text{=}CH_2$$

The unsaturated ester submitted to the catalytic cross-metathesis reaction with the pentenenitrile in the process according to the invention, is most preferably an unsaturated ester responding to formula (II)

$$R_1\text{—}O\text{—}C(O)\text{—}(CH_2)_m\text{—}CH\text{=}CH\text{—}R_2 \quad (II)$$

in which
$R_1$ is either H or a saturated alkyl group containing from 1 to 5 carbon atoms;
$R_2$ is either H or an alkyl group containing from 1 to 10 carbon atoms, either saturated or containing 1 or 2 unsaturations and bearing optionally a hydroxyl, a carboxylic or an ester group, and
m is equal to 7;
with the preference that $R_2$ is either H or an alkyl group containing from 1 to 10 carbon atoms, either saturated or containing 1 or 2 unsaturations and bearing optionally a hydroxyl, a carboxylic or an ester group, with a particular preference when $R_2$ is an alkyl group containing from 2 to 8 carbon atoms, either saturated or containing 1 or 2 unsaturations and bearing optionally a hydroxyl, a carboxylic or an ester group.

Examples of unsaturated esters responding to such preference are

Myristoleic esters responding to formula $$R_1\text{—}O\text{—}C(O)\text{—}(CH_2)_7\text{—}CH\text{=}CH\text{—}(CH_2)_3\text{—}CH_3$$

Palmitoleic esters responding to formula $$R_1\text{—}O\text{—}C(O)\text{—}(CH_2)_7\text{—}CH\text{=}CH\text{—}(CH_2)_5\text{—}CH_3$$

Oleic esters (cis isomer) or elaidic esters (trans isomer) responding to formula $$R_1\text{—}O\text{—}C(O)\text{—}(CH_2)_7\text{—}CH\text{=}CH\text{—}(CH_2)_7\text{—}CH_3$$

Methyl oleate responding to formula $$CH_3\text{—}O\text{—}C(O)\text{—}(CH_2)_7\text{—}CH\text{=}CH\text{—}(CH_2)_7\text{—}CH_3$$

Linoleic esters (cis isomer) or linoelaidic esters (trans isomer) responding to formula $$R_1\text{—}O\text{—}C(O)\text{—}(CH_2)_7\text{—}CH\text{=}CH\text{—}CH_2\text{—}CH\text{=}CH\text{—}(CH_2)_4\text{—}CH_3$$

α-Linolenic esters responding to formula $$R_1\text{—}O\text{—}C(O)\text{—}(CH_2)_7\text{—}CH\text{=}CH\text{—}CH_2\text{—}CH\text{=}CH\text{—}CH_2\text{—}CH\text{=}CH\text{—}CH_2\text{—}CH_3$$

Ricinoleic esters responding to formula $$R_1\text{—}O\text{—}C(O)\text{—}(CH_2)_7\text{—}CH\text{=}CH\text{—}CH_2\text{—}CH(OH)\text{—}(CH_2)_5\text{—}CH_3$$

Methyl ester of 9-decenoic acid of formula $$CH_3\text{—}O\text{—}C(O)\text{—}(CH_2)_7\text{—}CH\text{=}CH_2$$

Methyl ester of 9-undecenoic acid of formula $$CH_3\text{—}O\text{—}C(O)\text{—}(CH_2)_7\text{—}CH\text{=}CH\text{—}CH_3$$

Methyl ester of 9-dodecenoic acid of formula $$CH_3\text{—}O\text{—}C(O)\text{—}(CH_2)_7\text{—}CH\text{=}CH\text{—}CH_2CH_3$$

Esters of 9-octadecenedioic acid responding to formula $$R_1\text{—}O\text{—}C(O)\text{—}(CH_2)_7\text{—}CH\text{=}CH\text{—}(CH_2)_7\text{—}C(O)\text{—}O\text{—}R_1$$

The unsaturated ester submitted to the catalytic cross-metathesis reaction with the pentenenitrile in the process according to the invention, is particularly most preferably an unsaturated ester responding to formula (II)

$$R_1\text{—}O\text{—}C(O)\text{—}(CH_2)_m\text{—}CH\text{=}CH\text{—}R_2 \quad (II)$$

in which
$R_1$ is a saturated alkyl group containing from 1 to 5 carbon atoms;

$R_2$ is a saturated alkyl group containing 8 carbon atoms, and m is equal to 7.

In such particularly most preferred embodiment, the unsaturated ester is an oleic ester. Methyl oleate is particularly preferred.

Cis or trans isomer of the above-mentioned unsaturated esters of formula (II) or a mixture of cis and trans isomers can be used in the process according to the invention.

Unsaturated esters of formula (II) can be used in pure form or as a mixture. The unsaturated ester of formula (II) used in the catalytic cross-metathesis reaction of the process according to the invention advantageously contains from 70 to 100, preferably from 75 to 95 and more preferably from 80 to 90 weight % of the unsaturated ester. The rest of the mixture can be saturated (fatty) esters or unsaturated (fatty) esters having other chain length. An unsaturated ester particularly preferred is a mixture of fatty methyl ester comprising from 80 to 85 weight % of methyl oleate.

The unsaturated ester of formula (II) is advantageously purified before use, preferably by distillation, in order to avoid traces of water or of other impurities such as peroxides.

The unsaturated ester of formula (II) is advantageously obtained from vegetable oils containing fatty acids in the triglyceride form. Unsaturated (fatty) esters are advantageously produced by well-know transesterification process using methanol as reagent to give methyl (fatty) esters. Oleic (fatty) esters are the most preferred unsaturated (fatty) esters for the process according to the invention. Vegetable oils can be canola (also called rapeseed), safflower, flaxseed, sunflower, corn, olive, soybean, peanut, cottonseed, palm, castor or coconut. Typical conditions for the transesterification are (but limited to): 0.5-5 h, 45–80° C., 0.1 MPa, in methanol with methylate as catalyst.

The pentenenitrile used in the catalytic cross-metathesis reaction is chosen among 2-pentenenitrile (2-PN) or 3-pentenenitrile (3-PN).

2-PN can come from the manufacture of adiponitrile starting from butadiene where it is a by-product usually valorized as energy.

3PN can come from the manufacture of adiponitrile starting from butadiene where it is an intermediate.

Cis or trans isomers of the pentenenitrile or a mixture of them can be used in the process according to the invention.

The pentenenitrile is advantageously purified, preferably by distillation, before use. When the pentenenitrile is stored for long period, it is advantageous to purify it under inert atmosphere and to store it at low temperature (<40° C.) and avoiding light radiation contact.

The process according to the invention further comprises submitting the obtained ester-nitrile of formula (III) to a hydrogenation in order to obtain the amino ester of formula (I).

The hydrogenation is advantageously conducted by exposing the ester-nitrile of formula (III) to hydrogen gas in the presence of a hydrogenation catalyst.

The catalyst used for the hydrogenation can be any known catalysts. Advantageous, the catalyst used for the hydrogenation is a catalyst based on Pd, Pt, Ni, Cu, Co, Ru, Rh, Re, Ir or a combination thereof. The catalyst can be supported or not. In case it is supported, it is advantageously supported on carbon, silica or alumina. The metallic content for supported catalysts is advantageously between 0.1 to 40%, preferably between 0.1 to 10%, weight/weight. The Raney type catalysts containing Ni, Cu, Co associated or not with promoters can also be used for the hydrogenation step.

Preferably the catalyst is selected among Ni Raney, Co Raney, Pd on charcoal, Pt on charcoal or Cu on alumina, promoted or not.

The catalyst used for the hydrogenation can also be the same catalyst as the one used for the cross-metathesis reaction.

The temperature at which the hydrogenation takes place is advantageously comprised between 50 and 200° C. and preferably between 80 and 150° C.

The pressure at which the hydrogenation takes place is advantageously comprised between 2 and 100 bar of hydrogen and preferably between 10 and 50 bar.

The hydrogenation can be made in one step or in several steps. Preferably, the hydrogenation is made in one step.

Another aspect of the present invention concerns a method (M1) for the manufacture of an ester-nitrile responding to formula (III)

$$R_1\text{—O—C(O)—}(CH_2)_m\text{—CH=CH—}(CH_2)_p\text{—CN} \qquad (III)$$

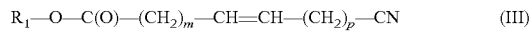

from an unsaturated ester responding to formula (II)

$$R_1\text{—O—C(O)—}(CH_2)_m\text{—CH=CH—}R_2 \qquad (II)$$

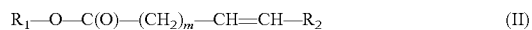

in which $R_1$ is either H or a saturated alkyl group containing from 1 to 5 carbon atoms, $R_2$ is either H or an alkyl group containing from 1 to 10 carbon atoms, either saturated or containing 1 or 2 unsaturations and bearing optionally a hydroxyl, a carboxylic or an ester group, m is equal to 7, 8, 9, 10 or 11, and p is equal to 0 or 1, said method (M1) comprising submitting the unsaturated ester of formula (II) to a catalytic cross-metathesis reaction with a pentenenitrile chosen among 2-pentenenitrile or 3-pentenenitrile in order to obtain the ester-nitrile responding to formula (III).

In the method (M1), the unsaturated ester of formula (II) is advantageously obtained by a reaction other than a catalytic cross-metathesis reaction.

In the method (M1), the unsaturated ester of formula (II) is advantageously obtained by a transesterification reaction using a triglyceride and an alcohol of formula $R_1OH$ as reagents, wherein $R_1$ is as previously defined, and/or by a hydrolysis reaction using the triglyceride and water as reagents.

Preferably, the triglyceride is extracted from a vegetable oil.

More preferably, the triglyceride is selected from the group consisting of canola, safflower, flaxseed, sunflower, corn, olive, soybean, peanut, cottonseed, palm, castor and coconut oils, and mixtures thereof.

Still another aspect of the present invention concerns a method (M2) for the manufacture of an amino ester of formula (I)

$$R_1\text{—O—C(O)—}(CH_2)_n\text{—NH}_2 \qquad (I)$$

in which $R_1$ is either H or a saturated alkyl group containing from 1 to 5 carbon atoms and n is an integer from 10 to 15, said method (M2) comprising submitting the ester-nitrile of formula (III) manufactured by the method (M1) as above described to an hydrogenation in order to obtain the amino ester of formula (I).

A last aspect of the present invention concerns the use of the amino ester of formula (I) prepared by the process as above described and/or by the method (M2) as above described for the manufacture of various useful chemical compounds.

Profitably, the amino ester of formula (I) prepared by the process as above described and/or by the method (M2) as above described is used for the manufacture of a polyamide, preferably by auto-polycondensing said amino ester. Then, a certain embodiment of the present invention is a process for the manufacture of a polyamide, which comprises manufacturing an amino ester by the process for the manufacture of the amino ester of formula (I) as above described and/or by the method (M2) as above described, and manufacturing the polyamide by auto-polycondensing said amino ester.

Thus, for example, the amino ester of formula (I) can be used as monomer for the manufacture of PA11, PA12, PA13, PA14, PA15 or PA16.

The amino ester of formula (I) can also be submitted to chemical reactions other than polycondensation reactions, leading to other chemical compounds such as dodecanediamine or dodecanedioic acid which can themselves be used as monomers for the manufacture of other polyamides such as PA12.x and PAy.12.

PA 12.x can therefore be made by the condensation of dodecanediamine obtained as described above with a species "x" which is an aliphatic dicarboxylic acid containing 4, 6, 8, 10, 11 or 12 carbons or an aromatic dicarboxylic acid such as terephthalic acid or furane dicarboxylic acid.

PA y.12 can there fore be made by the condensation of dodecanedioic acid obtained as described above with a species "y" which is an aliphatic diamine containing 4, 6, 8, 10, 11 or 12 carbons or an aromatic diamine such as paraphenylenediamine or furane diamine.

Compared the two processes leading to PA11 and P12 monomers according to prior art involving a highly complex synthesis, the process according to the invention is simpler with fewer steps than the previous processes and is therefore more cost competitive. Its implementation is also not governed by access to a specific raw material and the reagents used do not require expensive precautions for storage. Further, the embodiment of the process according to the invention involving a recycling of the co-products obtained presents the advantage that it does not coproduce many by-products that have to be upgraded separately. Finally, the process according to the invention has also the advantage of leading to mainly biosourced monomers.

Compared to the process according to FR 2912741 A1, the process according to the present invention presents the advantages of using nitrile compounds which are not CMR, which are less toxic and are further characterized by a lower vapor tension and higher flash point and boiling point rendering their use easier.

Another advantage of the process according to the invention is that it can involve as reactant, pentenenitriles which are produced in a large scale in the adiponitrile manufacture starting from butadiene raw material and which are available. Indeed, 2-pentenenitrile is a by-product of this process normally valorized as energy and 3-pentenenitrile is an intermediate for adiponitrile easily accessible with a good quality.

Further advantages of the process according to the invention is that the unsaturated esters of formula (II) are accessible raw materials because they are major compounds of natural oils, that they are biosourced and they are used as biodiesel (FAME—Fatty Acid Methyl Ester). In particular, on the contrary to ricinoleate which is solely made from castor oil, methyl oleate is one of the main components of vegetal transesterified oils.

The following examples are intended to illustrate the invention without however limiting the scope thereof.

General Procedure

All the examples were conducted under an inert atmosphere of argon using standard Schlenk tube techniques.

Grubbs catalyst 2nd generation, the formula of which is given below, was purchased from Aldrich and stored under argon.

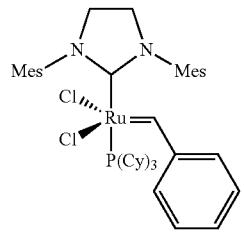

Hoveyda-Grubbs 2nd generation catalyst, of the formula below, was also used.

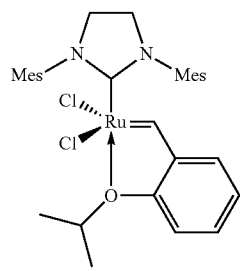

Methyl oleate was purchased from Oleon (initial purity 83%), dried by distillation, stored between 2 and 4° C. over a 4 A molecular sieves, degassed by argon bubbling and was protected from light.

Trans-3-pentenenitrile was provided by Aldrich (initial purity 95%) and was dried by distillation, stored between 2 and 4° C. over a 4 A molecular sieves, degassed by argon bubbling and was protected from light.

Cis 2-pentenenitrile was provided by Merck (initial purity 98%) and was dried by distillation, stored over 4 A molecular sieves, degassed by argon bubbling.

Anhydrous toluene was provided by Aldrich and degassed by argon prior to use.

The reactions were monitored using an Agilent 6850 gas chromatograph fitted with an HP-1 capillary column (40 m; 180 μm i.d; 0.70 μm film thickness). The temperature program was set up from 60° C. to 200° C. with 10° C./min then 200° C. to 230° C. with 2° C./min then 230° C. to 325° C. with 20° C./min. Injector temperature was 250° C. and detector temperature was 280° C. Helium was used as carrier gas and the injection volume was 1 μl.

EXAMPLE 1

In a Schlenk tube under argon, 6 mg (0.007 mmol; 0.06 mol %/methyl oleate) of Grubbs 2nd generation catalyst was weighted. Then 4.24 g (11.87 mmol) of distilled methyl oleate and 1.02 g (12.45 mmol) of distilled 3-pentenenitrile were added. The reaction mixture was stirred at 60° C. during 4 h at atmospheric pressure. Reaction mixture was then subjected to analysis. Methyl oleate conversion was 63%, 3-pentenenitrile conversion was 58% and C12 ester-nitrile selectivity was 41% (methyl oleate reference)

EXAMPLE 2

In a Schlenk tube under argon, 102 mg (0.120 mmol; 1 mol %/methyl oleate) of Grubbs 2nd generation catalyst was weighted. Then 4.25 g (11.90 mmol) of distilled methyl oleate and 1.01 g (12.33 mmol) of distilled 3-pentenenitrile were added. The reaction mixture was stirred at 60° C. during 4 h. Reaction mixture was then subjected to analysis Methyl oleate conversion was 76%, 3-pentenenitrile conversion was 80% and C12 ester-nitrile selectivity was 49% (methyl oleate reference)

EXAMPLE 3

In a Schlenk tube under argon, 101 mg (0.119 mmol; 1 mol %/methyl oleate) of Grubbs 2nd generation catalyst and 17.65 g of anhydrous toluene were weighted. Then 4.25 g (11.90 mmol) of distilled methyl oleate and 1.03 g (12.57 mmol) of distilled 3-pentenenitrile were added. The reaction mixture was stirred at 60° C. during 4 h. Reaction mixture was then subjected to analysis. Methyl oleate conversion was 78%, 3-pentenenitrile conversion was 77% and C12 ester-nitrile selectivity was 48% (methyl oleate reference).

EXAMPLE 4

In a Schlenk tube under argon, 101 mg (0.119 mmol; 1 mol %/methyl oleate) of Grubbs 2nd generation catalyst was weighted. Then 4.23 g (11.84 mmol) of distilled methyl oleate and 1.01 g (12.41 mmol) of distilled 2-pentenenitrile were added. The reaction mixture was stirred at 60° C. during 4 h. Reaction mixture was then subjected to analysis. Methyl oleate conversion was 70%, 2-pentenenitrile conversion was 54%, C11 ester-nitrile selectivity was 29% (reference methyl oleate)

EXAMPLE 5

In a Schlenk tube under argon, 102 mg (0.120 mmol; 1 mol %) of Grubbs 2nd generation catalyst and 17.85 g of anhydrous toluene were weighted. Then 4.26 g (11.93 mmol) of distilled methyl oleate and 1.01 g (12.41 mmol) of distilled 2-pentenenitrile were added. The reaction mixture was stirred at 60° C. during 4 h. Methyl oleate conversion was 79%, 2-pentenenitrile conversion was 86% and C11 ester-nitrile selectivity was 41% (reference methyl oleate)

EXAMPLE 6

In a Schlenk tube under argon, 2.12 g (10.58 mmol) of distilled methyl-10-undecenoate was weighted then 4.00 g (42.90 mmol) of distilled 2-pentenenitrile and finally 17.89 g of anhydrous toluene were added. Finally 5 mg (0.008 mmol; 0.07 mol %) of Grubbs 2nd generation catalyst was added. The reaction mixture was stirred 1 h at 100° C. and then subjected to analysis. Methyl-10-undecenoate conversion was 81%, 2-pentenenitrile conversion was 22%, C12 ester-nitrile selectivity was 96% (reference methyl-10-undecenoate).

EXAMPLE 7

In a Schlenk tube under argon, 8 mg (0.012 mmol; 1.2 mol %) of Hoveyda-Grubbs 2nd generation catalyst and 26.5 g of anhydrous dichloromethane were weighted. Then 0.36 g (1.02 mmol) of distilled methyl oleate and 0.19 g (2.34 mmol) of distilled 3-pentenenitrile were added. The reaction mixture was stirred at 40° C. during 4 h. Reaction mixture was then subjected to analysis. Methyl oleate conversion was 87%, 3-pentenenitrile conversion was 63% and C12 ester-nitrile selectivity was 50% (reference methyl oleate).

EXAMPLE 8

In a Schlenk tube under argon, 5 mg (0.008 mmol; 0.07 mol %) of Hoveyda-Grubbs 2nd generation catalyst was weighted. Then 4.2 g (11.8 mmol) of distilled methyl oleate and 1.0 g (12.2 mmol) of distilled 3-pentenenitrile were added. The reaction mixture was stirred at 60° C. during 4 h. Reaction mixture was then subjected to analysis. Methyl oleate conversion was 69%, 3-pentenenitrile conversion was 66% and C12 ester-nitrile selectivity was 50% (reference methyl oleate).

The invention claimed is:

1. A method for the manufacture of an ester-nitrile corresponding to formula (III)

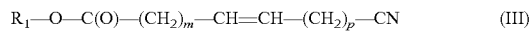

$$R_1-O-C(O)-(CH_2)_m-CH=CH-(CH_2)_p-CN \quad (III)$$

from an unsaturated ester responding to formula (II)

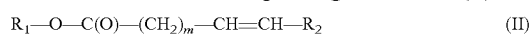

$$R_1-O-C(O)-(CH_2)_m-CH=CH-R_2 \quad (II)$$

in which
 $R_1$ is either H or a saturated alkyl group containing from 1 to 5 carbon atoms,
 m is equal to 7, 9, 10 or 11, and
 p is equal 1,
wherein
 when m is equal to 7, $R_2$ is an alkyl group containing from 2 to 8 carbon atoms, either saturated or containing 1 or 2 unsaturations and bearing optionally a hydroxyl, a carboxylic or an ester group;
 when m is equal to 9, $R_2$ is a saturated alkyl group containing from 6 to 8 carbon atoms;
 when m is equal to 10, $R_2$ is a saturated alkyl group containing 5 carbon atoms; and
 when m is equal to 11, $R_2$ is a saturated alkyl group containing 8 carbon atoms;
said method comprising submitting the unsaturated ester of formula (II) to a catalytic cross-metathesis reaction with 3-pentenenitrile in order to obtain the ester-nitrile responding to formula (III).

2. The method according to claim 1, wherein the unsaturated ester of formula (II) is obtained by a reaction other than a catalytic cross-metathesis reaction.

3. The method according to claim 1, wherein the unsaturated ester of formula (II) is obtained by a transesterification reaction using a triglyceride and an alcohol of formula $R_1OH$ as reagents, with $R_1$ as defined, and/or by a hydrolysis reaction using the triglyceride and water as reagents.

4. The method according to claim 3, wherein the triglyceride is extracted from a vegetable oil.

5. A method for the manufacture of an amino ester of formula (I)

$$R_1-O-C(O)-(CH_2)_n-NH_2 \quad (I)$$

in which $R_1$ is either H or a saturated alkyl group containing from 1 to 5 carbon atoms and n is an integer from 10 to 15,
said method comprising submitting the ester-nitrile of formula (III) manufactured by the method according to claim 1 to an hydrogenation in order to obtain the amino ester of formula (I).

6. The method according to claim 4, wherein the vegetable oil is selected from the group consisting of canola, safflower, flaxseed, sunflower, corn, olive, soybean, peanut, cottonseed, palm, castor and coconut oils, and mixtures thereof.

7. A process for the manufacture of a polyamide, the process comprising manufacturing an amino ester by the process according to the method according to claim 5, and manufacturing the polyamide by auto-polycondensing said amino ester.

8. The method according to claim 1, wherein m is equal to 9, 10 or 11.

9. The method according to claim 1, in which m is equal to 7, R1 is a saturated alkyl group containing from 1 to 5 carbon atoms and R2 is a saturated alkyl group containing 8 carbon atoms.

* * * * *